United States Patent [19]

Chesterfield et al.

[11] Patent Number: 5,374,278
[45] Date of Patent: * Dec. 20, 1994

[54] METHOD AND APPARATUS FOR HEAT TIPPING SUTURES

[75] Inventors: Michael P. Chesterfield, Norwalk; Stanley J. Malinowski, Guilford; George R. Proto, West Haven; Jonathan Wilson, Fairfield, all of Conn.

[73] Assignee: United States Surgical Corporation, Norwalk, Conn.

[*] Notice: The portion of the term of this patent subsequent to Oct. 20, 2009 has been disclaimed.

[21] Appl. No.: 962,947

[22] Filed: Oct. 19, 1992

Related U.S. Application Data

[63] Continuation-in-part of Ser. No. 436,439, Nov. 14, 1989, Pat. No. 5,156,788.

[51] Int. Cl.$^5$ .............................................. A61B 17/06
[52] U.S. Cl. ..................... 606/228; 606/148; 264/157
[58] Field of Search ................ 606/139, 148, 228–231; 289/1.2; 264/157

[56] References Cited

U.S. PATENT DOCUMENTS

| | | |
|---|---|---|
| 1,665,216 | 4/1928 | Morton et al. . |
| 2,012,776 | 8/1935 | Roeder . |
| 2,280,603 | 4/1942 | Plambeck . |
| 2,296,394 | 9/1942 | Meloon . |
| 2,578,889 | 10/1951 | Kennedy . |
| 2,847,703 | 8/1958 | Schrenk et al. . |
| 2,975,474 | 3/1961 | Smith . |
| 2,990,575 | 7/1961 | Gibbins et al. . |
| 3,020,120 | 2/1962 | Loliger . |
| 3,254,145 | 5/1966 | Tanguay . |
| 3,422,181 | 1/1969 | Chirgwin, Jr. . |
| 3,491,418 | 1/1970 | Nicita et al. . |
| 3,531,561 | 9/1970 | Trehu . |
| 3,574,804 | 4/1971 | Joonase . |
| 3,651,204 | 3/1972 | Nichols et al. . |
| 3,769,396 | 10/1973 | Espinosa . |
| 3,839,524 | 10/1974 | Adams et al. . |
| 3,875,946 | 4/1975 | Duncan . |
| 3,890,975 | 6/1975 | McGregor . |
| 3,926,194 | 12/1975 | Greenberg et al. . |
| 4,443,215 | 4/1984 | Smith . |
| 4,832,025 | 5/1989 | Coates . |
| 5,007,922 | 4/1991 | Chen et al. . |
| 5,080,667 | 1/1992 | Chen et al. . |

FOREIGN PATENT DOCUMENTS

| | | |
|---|---|---|
| 0477020 | 3/1992 | European Pat. Off. . |
| 1478695 | 3/1967 | France . |
| 2361119 | 3/1978 | France . |
| 1588031 | 4/1981 | United Kingdom . |

OTHER PUBLICATIONS

Graumont and Hensel, Encyclopedia of Knots and Fancy Ropework, Cornell Maritime Press, N.Y. 1945, pp.: preface, 11, 14–17, 84–85, 630, 632, 635 and 639.
Loop Ligature and Knot Ligature Laparoscopic Surgical Sutures, American Surgical Instruments, Inc., Surgical Laparoscopy & Endoscopy, vol. 1, No. 1, Mar. 1991.
Basic Sailing, The American National Red Cross, 1966.
Piloting, by Chapman, 1983.

*Primary Examiner*—Stephen C. Pellegrino
*Assistant Examiner*—Jeffrey A. Schmidt

[57] ABSTRACT

A heat tipping method and apparatus for surgical sutures to facilitate inserting the sutures into the barrel ends of surgical needles. The method comprises tensioning the suture, heating a portion of the suture to be heat tipped by blowing a current of hot air across the portion of the suture, and releasing the tension and cutting the portion of the suture to create heat tipped ends. The apparatus comprises a cylindrical drum around which the suture is wound, a concave channel in the drum for delimiting a portion of the suture to be heated, and hot air blowers for heating the delimited portions of the suture to a heat tipping temperature. In another embodiment, the suture is looped and knotted. The loop and/or knot is then heated under such conditions so as to reversibly stiffen the loop and/or knot. Such stiffening facilitates placement and securement of the suture loop during surgical procedures.

21 Claims, 16 Drawing Sheets

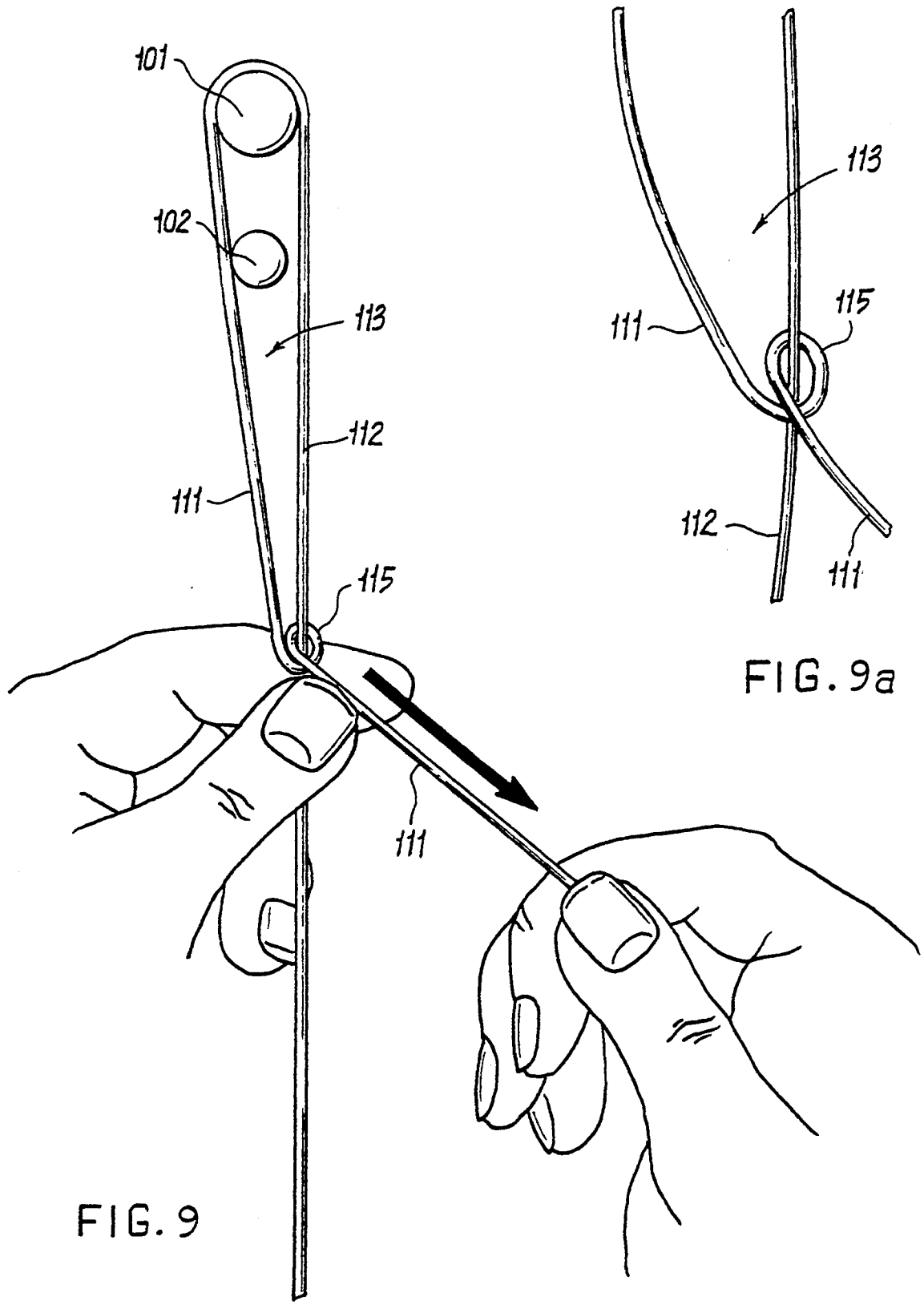

METHOD AND APPARATUS FOR HEAT TIPPING SUTURES

This is a continuation-in-part of U.S. application Ser. No. 07/436,439 filed Nov. 14, 1989, now issued as U.S. Pat. No. 5,156,788.

BACKGROUND OF THE INVENTION

1. Field of the Invention

This invention relates to surgical sutures and in particular to a surgical suture with a treated loop end for use in surgical procedures and a treatment method therefor.

2. Background of the Art

Surgeons often use needles with attached sutures in surgical operations. A typical needle-suture combination is shown in FIG. 1. Generally, such needle suture combinations comprise a non-eyed needle with a cylindrical hole in a barrel shaped rear end for receiving a suture, and a suture with a treated end which is received into the hole. Provided with a needle-suture combination, operating room personnel need not waste time trying to thread an eyed needle with a suture. After using the needle-suture combination to close a wound the surgeon may detach the needle either by cutting the suture or by pulling on the needle with sufficient force to detach the needle from the suture.

In making needle-suture combinations, whether the needles be eyed or non-eyed, it is generally necessary to treat the tip of the suture in some manner in order to make it easier to insert the tip into the barrel end of the needle. Braided or woven sutures especially have a tendency to "broom" or flare out at the ends. The purpose of the treatment is to stiffen the tip of the suture, as, for example, the end of a sewing thread is wetted and twisted so that it may be inserted into the eye of a sewing needle. With regard to surgical sutures, this "tipping" process generally has been accomplished by coating and/or soaking the end of the suture with a solution of a resinous tipping solution. One such solution is Mariotte mixture, which comprises a solution of polyamide resin in isopropyl alcohol and water. Another such solution is Gould mixture, which comprises a solution of polyamide resin in methanol.

Generally a suture to be tipped is first placed under tension to reduce slack so that it may be maintained in a predetermined position on a drum or other suture holding device. Optionally, the tension may be such as to reduce the diameter of the suture. The suture is then dipped into the tipping solution and allowed to dry while under tension. The sutures are then warmed in a drying oven at about 225° F. for about 10 minutes to dry the sutures. After drying the sutures can be cut and released from tension. The process results in a tipped end on each side of a cut. In cases where tension has optionally been employed to reduce the suture diameter, release of said tension will allow the suture to expand to its original diameter except at the tipped end portion. This can facilitate insertion of the end into a needle. A method for making a needle-suture combination wherein the suture end has been treated with resin solutions is described in U.S. Pat. Nos. 3,980,177 and 3,890,975.

Although dipped sutures prepared in accordance with the above procedures have been used successfully, there are several drawbacks with the use of tipping solutions. The main problems are those of consistency and controllability. Non-uniform solvent evaporation, caused by variations in oven temperature and heating time, result in uneven diameter reduction and inconsistency of tipping. Furthermore, the dried residue of polymer left after evaporation can flake off or develop cracks.

A further drawback in these known procedures is that the suture is permanently altered. After the suture has been inserted into a needle there is no need for it to be stiffened. A limp suture will lay in the position in which the surgeon leaves it, whereas a stiff suture can interfere with the suturing operation. Nevertheless, a suture tipped by the prior art solutions will always have a portion containing the stiff residue of included polymer resin.

Other suture configurations can benefit from non-permanent stiffening. Untreated pre-looped or pre-knotted suture-ligatures, for example, are typically limp and hard to handle. Additionally, the knot may undesirably slip either before or after the loop is tightened. Permanent stiffening of these suture-ligatures can interfere with the surgeon's ability to tighten the loop or interfere with the ability of the knot to hold position. Therefore, it would be advantageous to have a looped suture-ligature having a reversibly stiffened loop and or knot to enhance handling characteristics and or prevent undesirable knot slippage.

Heating of certain filaments is known in the art. A method for heat setting of stretch oriented polyglycolic acid filaments is disclosed in U.S. Pat. No. 3,422,181. This patent discloses a method for improving the strength retention and absorption rate of a polyglycolic acid filament to be used in a suture by subjecting the filament to dry heat at a relative humidity of not greater than 20% and at a temperature of between 50° C. and 190° C.

Another method which has been employed for treating sutures involves melt fusion, as described in U.S. Pat. No. 4,832,025, issued to Coates. The suture is heated to a temperature at least high enough to "melt fuse" a portion of the outer filaments of the multifilament suture. Such temperature is typically about 260° C. to 300° C. (500° F. to 572° F.). The suture stiffens upon cooling. Surface melting of the outer filaments has the effect of holding the filaments together when the suture is cut. It also causes stiffening of the suture which facilitates insertion of the suture end into the drilled hole of a needle. However, the melt fusion of suture has significant drawbacks.

Firstly, the melt fusion of filaments weakens the suture, whose tensile strength is degraded in proportion to the extent of melt fusion.

Secondly, melt fusion causes an irreversible change in the filaments which results in permanent stiffening and permanent loss of tensile strength.

Thirdly, with the temperatures required for melt-fusion an inconveniently short heating cycle is required. For example, for a size 3/0 silicone coated polyester suture heated to between 260° C. to 300° C. in a 4 mm. diameter heating tunnel, the heating time is no more than about 3 seconds. Short heating times at such high temperature allow for more inconsistency and variation in the results of the tipping process than longer heating times.

Yet another method for treating the tips of sutures is described in U.S. Pat. Nos. 5,007,922 and 5,080,667 issued to Chen. Chen's method includes heating a portion of a monofilament suture to approximately 300° F.

for about five minutes. The heated portion of the monofilament is then drawn to reduce its diameter. Subsequent cutting of the drawn portion creates two suture tips on either side of the cut.

The prior known methods for tipping are, therefore, unsatisfactory. What is needed is a method for treating sutures which facilitates reversible stiffening of the suture without loss of tensile strength. Not only would such a treatment method be useful for tipping, it would also be useful in any application where a suture is more easily handled when temporarily stiffened. For example, sutures are often sold in a pre-looped and knotted configuration. It would be advantageous to reversibly stiffen looped and/or knotted sutures prior to use to facilitate their application in surgical procedures.

SUMMARY OF THE INVENTION

A method is disclosed for heat tipping sutures which is fully reversible and which causes substantially no loss of tensile strength. Heat tipping cycle times associated with the method of the present invention are of such duration to bring about evenness and consistency of results. The heat tipping method provided herein comprises delimiting a portion of the suture to be heat tipped, and heating the delimited portion of the suture to a heat tipping temperature and maintaining said temperature for a period of time, the heat tipping temperature being such as to cause the portion of the suture to be reversely stiffened upon cooling.

In another embodiment, the present invention includes a method for reversibly stiffening a looped and knotted suture. The method comprises heating the looped and/or knotted portion of the suture to a predetermined temperature and maintaining the temperature for a period of time sufficient to cause the suture loop and/or knot to be reversibly stiffened upon cooling.

The suture is looped and knotted by forming a loop in the suture and then forming a slidable knot to secure said loop. The knot is tied by passing the first end (the running end) of the suture around the second end portion (the standing part of the suture) and through the loop to form a turn, then making at least 1 and preferably from about 2 to about 6 turns of the running end around the loop forming portions of both the running end and standing parts of the suture, and finishing the knot with a half-hitch.

The loop and knot are formed with the aid of a mandrel means and a heat source accomplishes the reversible stiffening by directing a stream of air at 300° F. to 320° F. across the looped and knotted portion of the suture.

BRIEF DESCRIPTION OF THE DRAWINGS

FIGS. 7 to 18 illustrate sequentially the steps for tying the knot of the present invention.

DETAILED DESCRIPTION OF THE INVENTION

Figure 1:
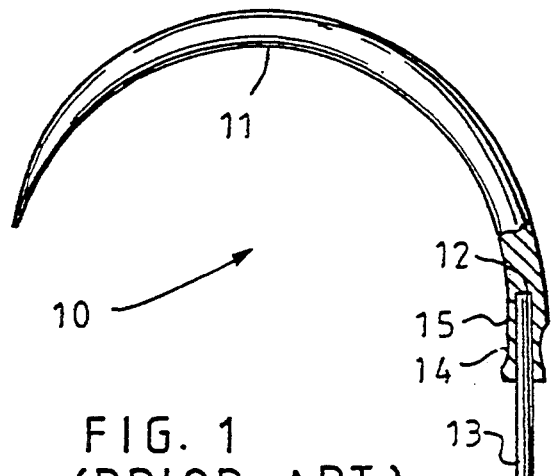
FIG. 1 illustrates a prior art needle-suture combination with a non-eyed needle.

FIG. 1 illustrates a typical needle-suture combination 10 of the prior art. Needle 11 has a barrel shaped end 15 with a cylindrical hole 12 for receiving the end of suture 13. Once the suture is inserted a crimp 14 is put into the barrel to retain the suture. A needle-suture combination and methods and instrumentation for making such combination are disclosed in U.S. Pat. No. 3,980,177.

Figure 1A:
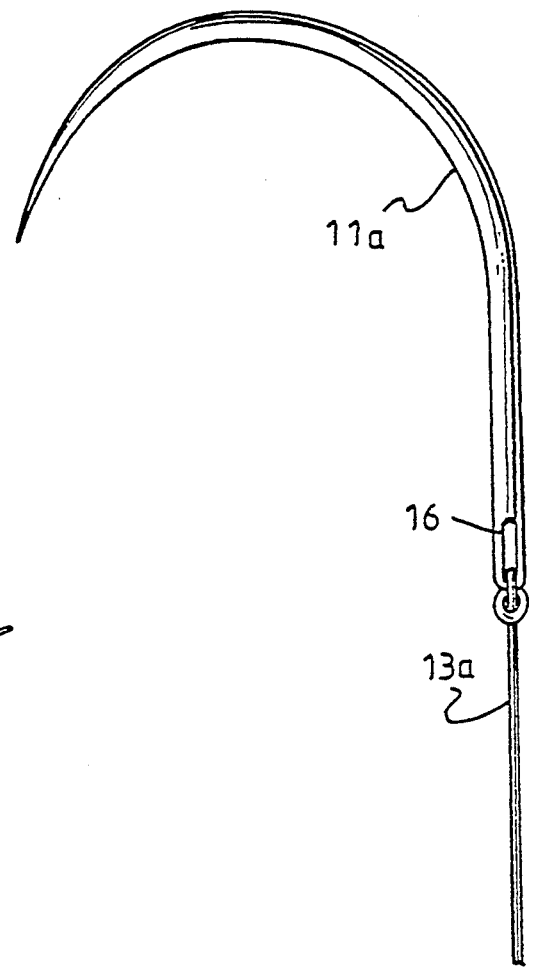
FIG. 1a illustrates a prior art needle-suture combination with an eyed needle.

FIG. 1a illustrates a prior art eyed needle and suture combination. Needle 11a contains eye 16 through which suture 13a is threaded.

The heat tipping method of the present invention produces a suture which is reversibly stiffened. The heat tipped suture is stiff enough to be inserted into the barrel or eye of a surgical needle without brooming, but simple manipulation, such as bending and unbending the suture for example by drawing the fingers along the suture, will restore the flexibility and normal limpness of the suture as well as the original diameter if the diameter had been reduced by tensioning. This characteristic, i.e. reversible stiffening, is highly advantageous since there are no unwanted after effects from the tipping process such as residual stiffness or polymer residue, and it is not achieved by the prior an processes which fuse the surface filaments or glue them together with polymer resins.

Figure 2:
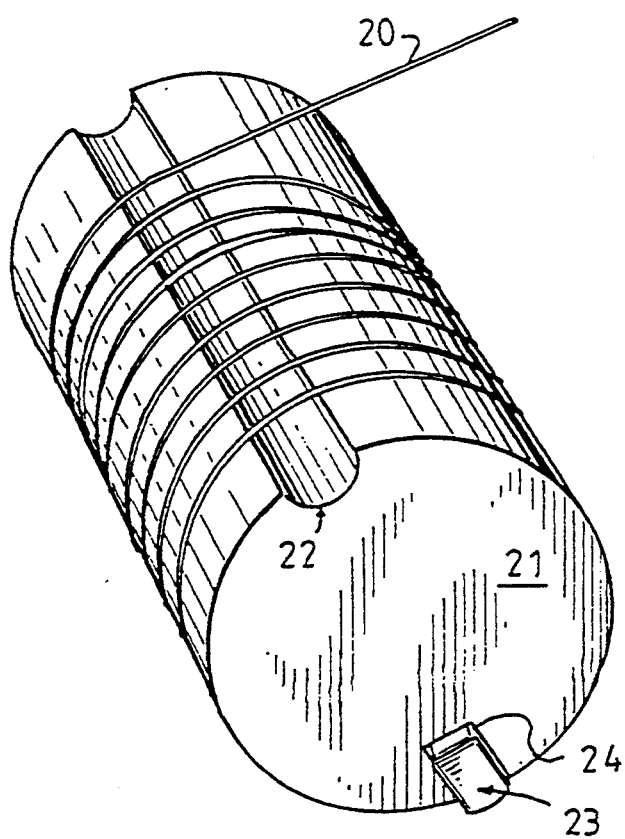
FIG. 2 is a perspective view of suture wound around a heat tipping apparatus constructed according to the present invention.
Figure 3:
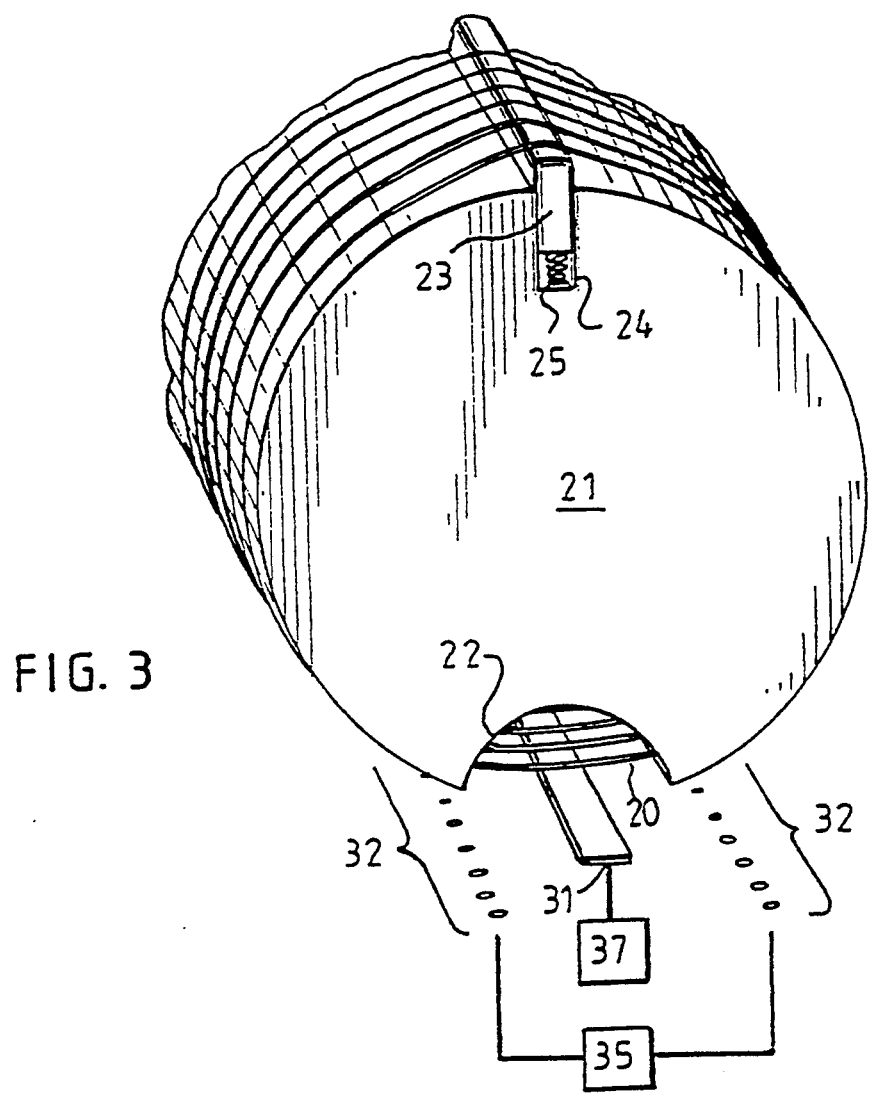
FIG. 3 illustrates the heat tipping drum positioned for the heat tipping procedure.

Referring to FIGS. 2 and 3, a preferred method is disclosed for heat tipping sutures. The first step of the preferred heat tipping method of the present invention is to wind the suture around a cylindrical drum, preferably under tension so that there is no loose slack. Optionally, greater tension may be applied to reduce the suture diameter.

Suture 20 is wound around cylindrical drum 21. The drum is preferably constructed from metal, e.g., stainless steel, although other materials of construction, such as plastics, may be employed. The circumference of the drum may be chosen in accordance with the intended length of the individual sutures after cutting. Means for winding sutures under tension are conventional in the art.

Drum 21 has a concave channel or groove 22 which extends longitudinally along the surface of the drum 21 in an orientation parallel to the axis of the drum 21 and transverse to the orientation of the suture 20. The concave channel 22 provides a means for delimiting the portion or section of the suture to be heat tipped. As can be seen from FIGS. 2 and 3, the sutures 20 are stretched transversely across the mouth of the concave channel 22. The delimited portion of the suture is exposed for heating. The delimited portion is held in close contact with the cylindrical drum 21, which is preferably made of thermally conductive metal and which therefore provides some protection of the non-delimited portion of suture 20 from heating by conducting heat away from said undelimited portion. Different widths of concave channel 22 will result in different lengths of tipped portions of the suture.

Drum 21 optionally comprises a means for varying the effective circumferential distance of drum relative to the suture. Changing the effective circumference of the drum provides a means for applying tension to the suture or reducing tension.

Referring to FIG. 3, the circumference adjusting device is preferably an elongated member or bar 23 which is mounted within a longitudinally extending notch 24 in the surface of drum 21. The bar 23 is movable radially between a position wherein the bar extends a relatively further distance beyond the surface of the drum (thereby presenting an effectively larger drum circumference to the suture and increasing suture tension) and a position wherein the bar extends a relatively lesser distance, or not at all, beyond the surface of the drum. In the last mentioned position, the bar presents an effectively smaller drum circumference to the suture and lessening suture tension.

After the suture has been wound around the drum as shown, the drum is positioned in a heat treating apparatus as diagrammed in FIG. 3. The drum 21 is mounted above an elongated heating outlet 31 supplied by a source of hot air 37 shown schematically in FIG. 3. Thus the portions of the sutures 20 to be heat tipped are arrayed in alignment over the heating outlet 31. On each side of the heating outlet 31 there is a parallelly extending line of cool air outlets 32. Heat tipping is optimally accomplished by blowing hot air from outlet 31 across the sutures 20. For this reason, the depth of channel 22 should be sufficient to accommodate adequate flow of the heated air past the delimited portions of the suture.

A source of cool air 35 shown schematically in FIG. 3 communicates with cool air from outlets 32 to provide a wall of cool air which protects the remaining portions of the sutures from inadvertent heating. The heat tipping process is optimally accomplished by providing a flow of hot air at a heat tipping temperature, which is defined as that temperature which causes a suture to be reversibly stiffened upon cooling to ambient or room temperature. Heat tipping is delimited by variables of temperature of air flow, duration of heating time, and suture diameter. A larger suture diameter requires a longer heating time, and a higher heating temperature requires a shorter heating time. The heat tipping temperature is at least high enough to cause some alteration in either the macroscopic structure or the molecular structure of the suture material, but it should not be so high as to cause melting or deterioration of the suture. The optimum heat tipping temperature range is from about 300° F. to about 320° F. Of the three parameters of heat tipping—temperature, time, and suture diameter—it is best to hold temperature constant. Heat tipping is optimally done at 300° F. to 320° F. for all suture diameters with an adjustment of heating time in accordance with suture diameter. Temperatures lower than about 295° F. produce no heat tipping, or require long periods of heating, whereas temperatures above about 330° F. may cause structural damage to the suture, or are associated with heating times which are too short to control easily.

Table I below sets forth a tabulation of heating times for various size sutures at the preferred heat tipping temperature of about 320° F. As can be seen from Table I, the heating times range from 12 to 16 seconds for size 5/0 sutures, to about 60 to 65 seconds for size 2 sutures. These heating times allow the heat to transfer through the suture evenly and without localized inconsistencies caused by hot spots.

TABLE I

| Copolymer of Glycolide and Lactide Type Suture Heat Tipping Temperature = 320° F. | |
|---|---|
| Suture Size | Heating Time (seconds) |
| 2 | 60–65 |
| 1 | 50–55 |
| 1/0 | 42–46 |
| 2/0 | 25–30 |
| 3/0 | 22–28 |
| 4/0 | 14–18 |
| 5/0 | 12–16 |

Figure 4:
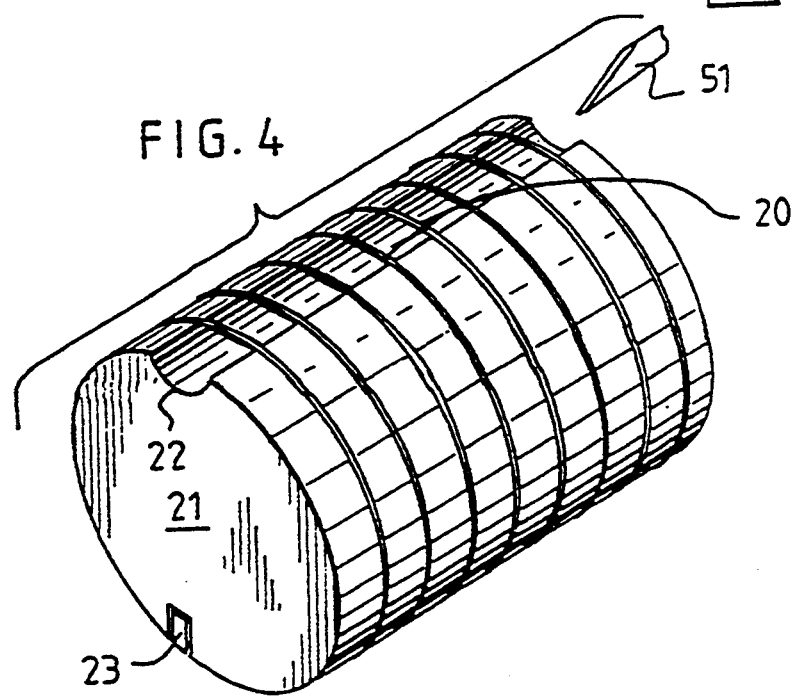
FIG. 4 illustrates the cutting operation.
Figure 5A:
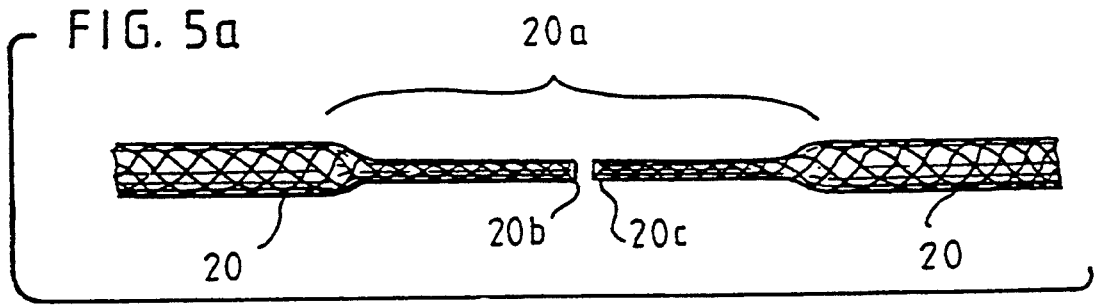
FIGS. 5a and 5b are side views of a heat tipped suture with and without diameter reduction, respectively.
Figure 5B:
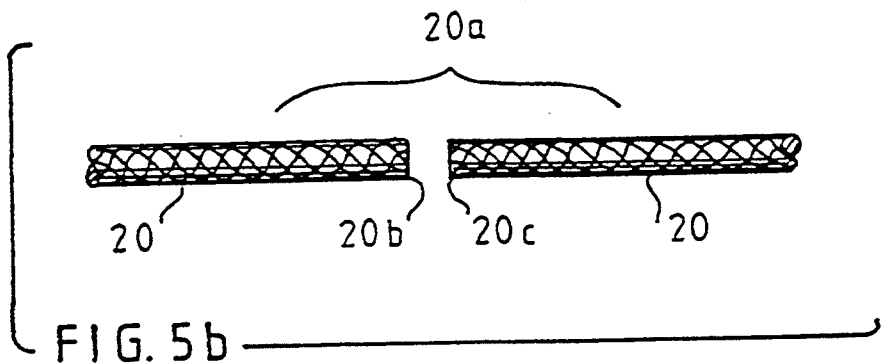

Referring to FIGS. 4, 5a and 5b, after the heating is completed the suture 20 (90% glycolide/10% lactide) is allowed to cool to ambient or room temperature and the diameter modifier 23 is depressed to reduce tension. A knife 51 is drawn laterally across the heat tipped portion of the sutures 20a thereby cutting them and creating two heat tipped ends, 20b and 20c, at each cut. In cases where the suture diameter has been reduced through tensioning, it should be noted that when the tension is released the suture will expand to its original diameter except at the heat tipped portion 20a, which retains the smaller diameter of the tensioned suture, as shown in FIG. 5a. When the suture has not been tensioned so as to reduce its diameter the heat tipping process of the present invention will nevertheless facilitate insertion of the tipped end into a needle by stiffening the end and by preventing brooming of the braided filaments, as illustrated in FIG. 5b.

The heat tipped portion 20a provided in accordance with the present invention is stiff and is easily insertable into the barrel end of a surgical needle. Braided sutures which are heat tipped will not "broom" or expand. The heat tipped portion may be restored to substantially its original flexibility and limpness by manipulating it. e.g. running it through one's fingers while bending and curling it.

Heat tipping according to the present invention may be performed on a variety of suture materials such as, but not limited to, polymers and copolymers of glycolide and lactide, polydioxanone, collagen, silk, nylon, dacron, cotton, linen, etc., preferably braided.

Figure 6:
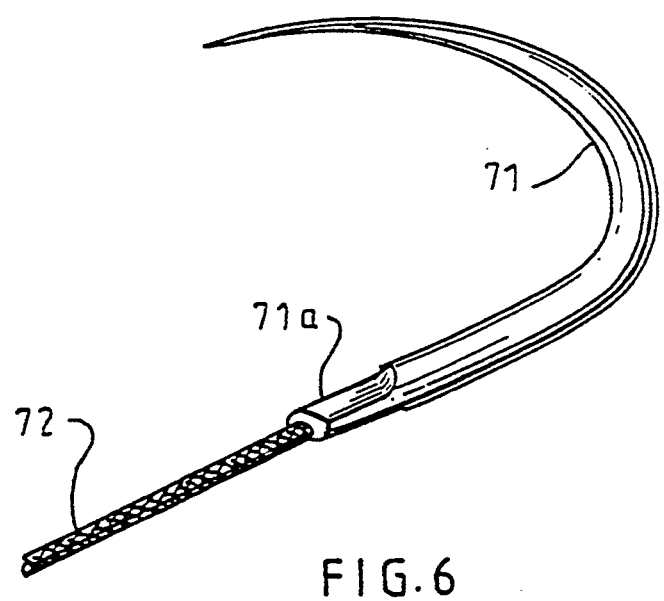
FIG. 6 is a perspective view of a combination of a needle and a heat tipped suture.

FIG. 6 illustrates a needle suture combination employing a suture prepared in accordance with the present invention. Needle 71 has a barrel end 71a into which heat tipped braided suture 72 is inserted. The suture is fixed by crimping or swaging the barrel end as illustrated.

A further application of the heat treatment method of the present invention relates to the reversible stiffening of a suture loop.

Pre-looped sutures and instruments for applying them are disclosed in U.S. Pat. Nos. 3,476,114, and 3,476,115, both of which are hereby incorporated by reference. Such instruments generally include an elongated tubular body member which carries a ligature (suture) within its shaft, the ligature terminating in an external loop which is intended to be drawn tightly about a severed vessel to achieve hemostasis.

Modern suture making technology is capable of producing sutures of bioabsorbable and non-bioabsorbable materials with great smoothness and flexibility, including multifilament braided sutures. It would facilitate surgical procedures, though, if a pre-looped suture were at least initially somewhat stiff so as to facilitate handling and placement of the loop. It would also be advantageous if the knot were at least initially somewhat stiff so as to lessen the possibility of its unravelling, loosening or slipping prior to or during placement. The heat treatment method described herein provides the means to accomplish these objectives.

Figures 7, 7A:
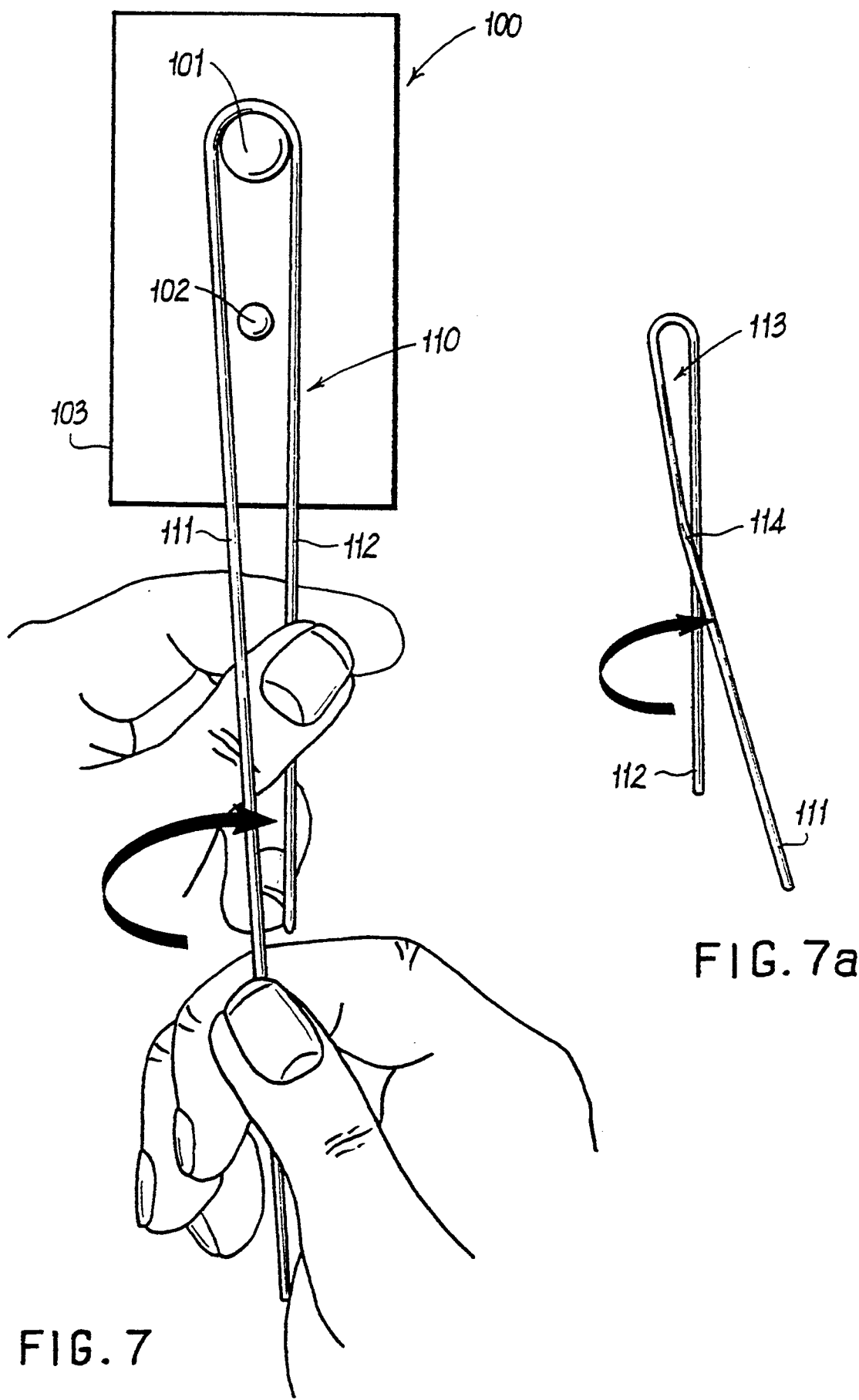

Referring to FIGS. 7 and 7a, a mandrel 100 includes upright and optionally parallel members 101 and 102 supported by frame 103. Suture 110 can be fabricated from bioabsorbable material or non-bioabsorbable material, and may be monofilament, or multifilament and braided, twisted or otherwise fabricated. Preferred bioabsorbable materials for suture fabrication include collagen, and synthetic polymers such as homopolymers and copolymers of glycolide, lactide, caprolactone, and p-dioxanone, trimethylene carbonate and combinations thereof. Preferred non-bioabsorbable materials include silk, cotton, linen and synthetic polymers such as nylon, Dacron (DuPont) and polypropylene.

The suture knot described below is a surgical hitch knot for tying off body tissue and the like during an operation. The surgical hitch comprises a primary loop, at least one round turn of the running end of the suture around the standing part, followed by at least one (and preferably from 2 to about 6) intermediate turns of the running end around the loop forming portion of both the running end and the standing part, and terminated with a half-hitch formed around the standing part. The tying of the surgical hitch may be varied in accordance with the material and the type of constructions of the suture. Thus, smooth and slippery sutures (e.g., monofilaments and finely braided sutures) may require more intermediate turns than a rougher suture for optimum performance of the surgical hitch. A knot suitable for most types of sutures may be fabricated as follows:

Suture 110 is passed around member 101 as illustrated thereby forming a bight and defining suture portions 111, the running end, and 112 the standing part. Suture portion 111 is then crossed over suture portion 112 at crossover point 114 to form primary loop 113.

Figures 8, 8A:
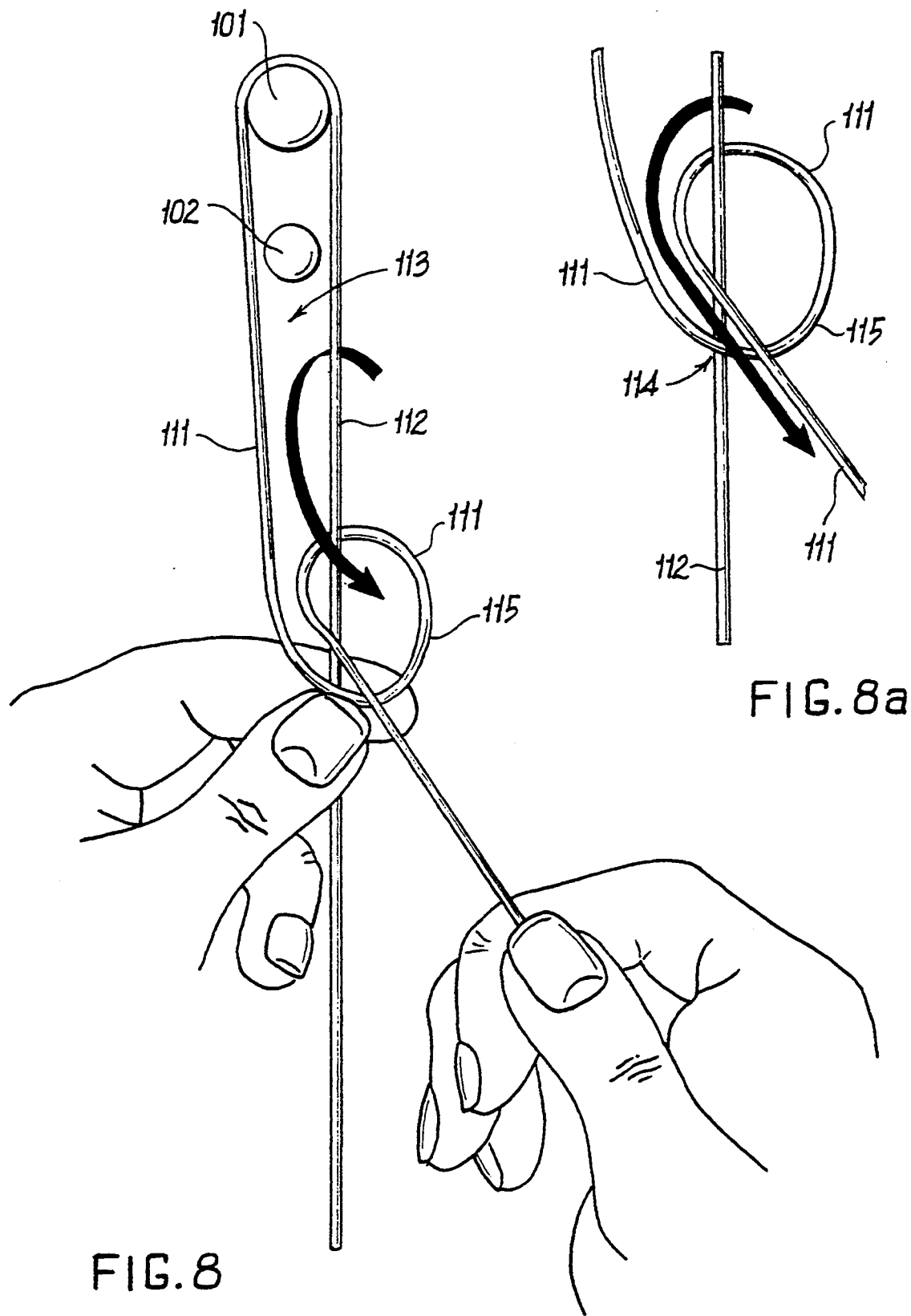

Referring to FIGS. 8 and 8a, suture portion 111 is then passed around and under suture portion 112, and up through primary loop 113 between the loop forming sections of portions 111 and 112 to form a first turn 115. Suture portion 111 is then pulled taut, as shown in FIGS. 9 and 9a.

Figures 10, 10A:
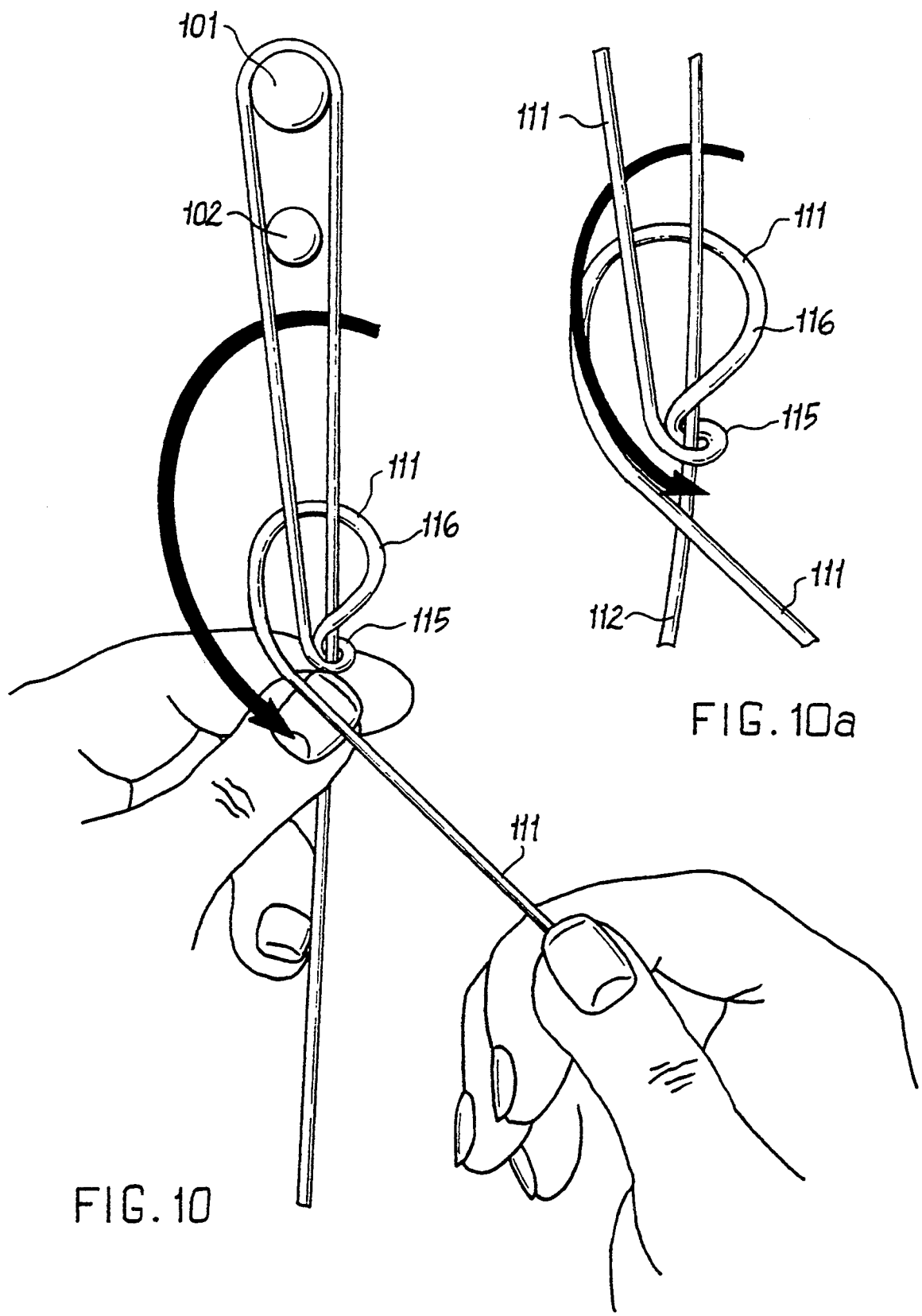
Figure 11A:
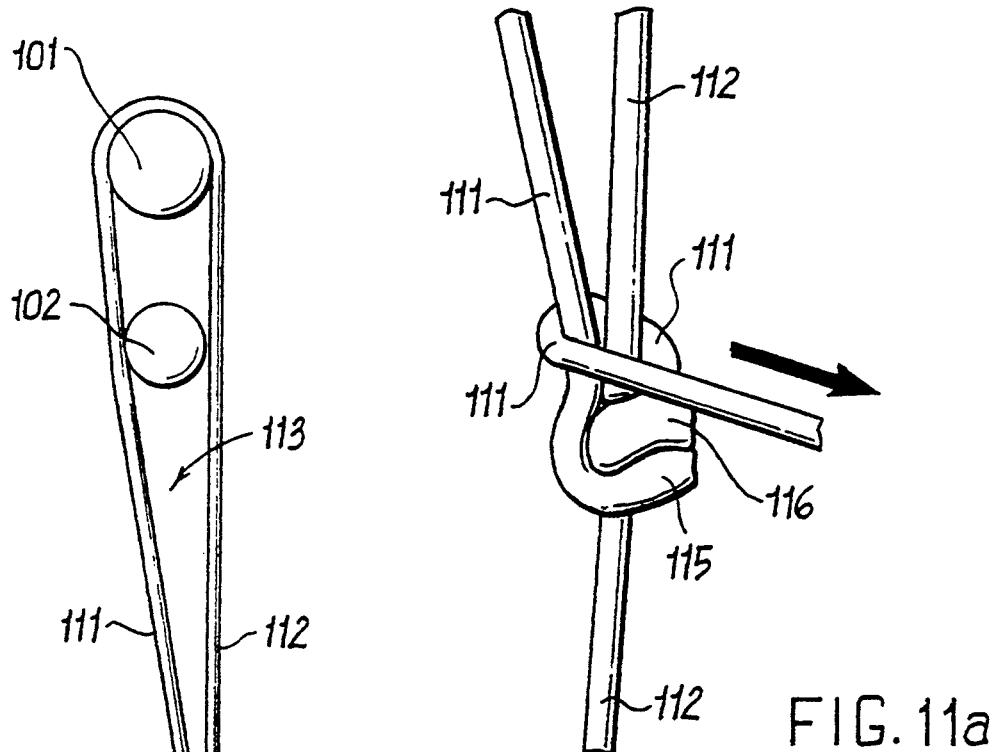
Figure 11:
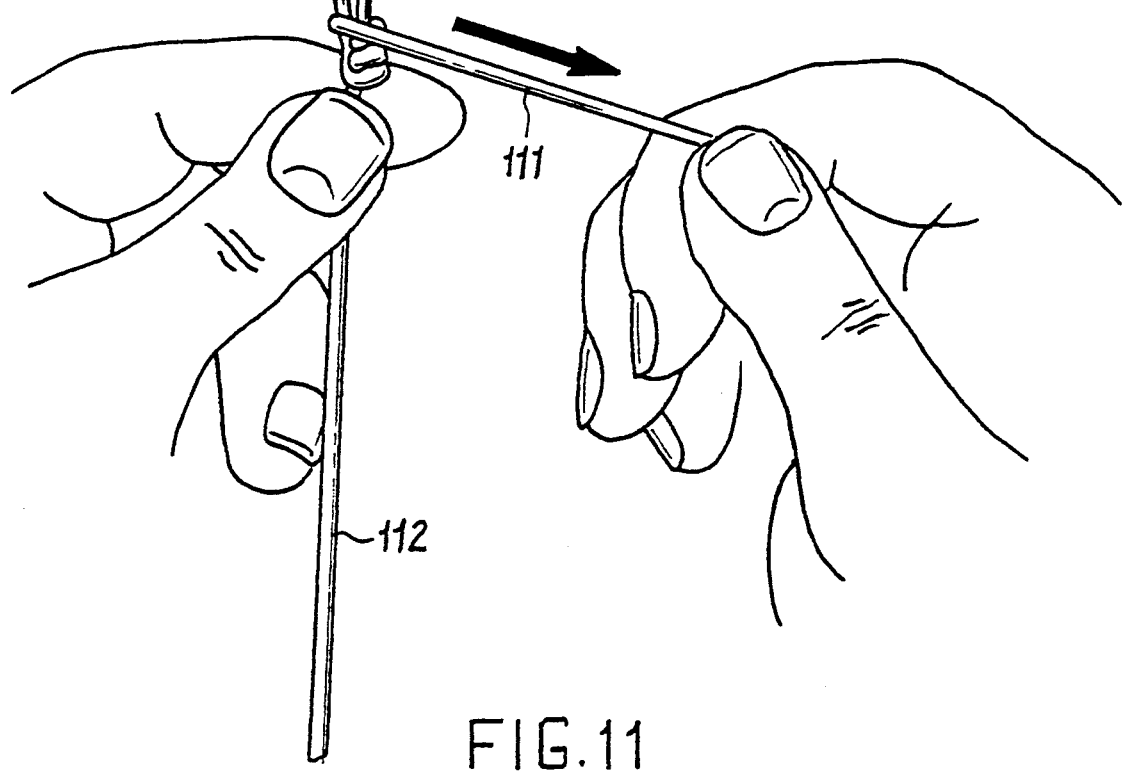

Referring to FIGS. 10 and 10a, the suture portion 111 is then brought around and under the primary loop forming sections of both portions 111 and 112, and crossed over the top of the knot to form a second turn 116. Suture portion 111 is then pulled taut as shown in FIGS. 11 and 11a.

Figures 12, 12A:
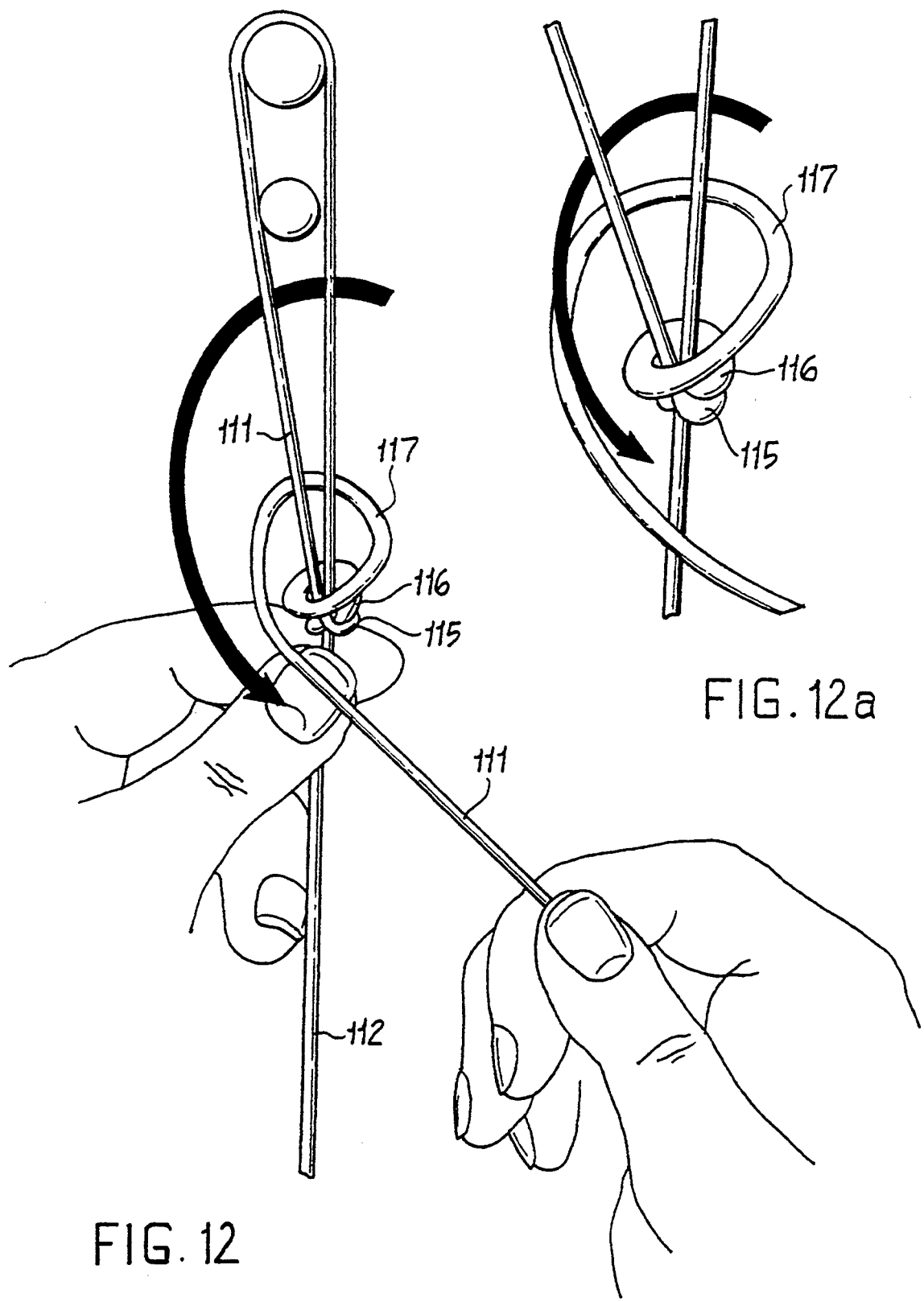
Figures 13, 13A:
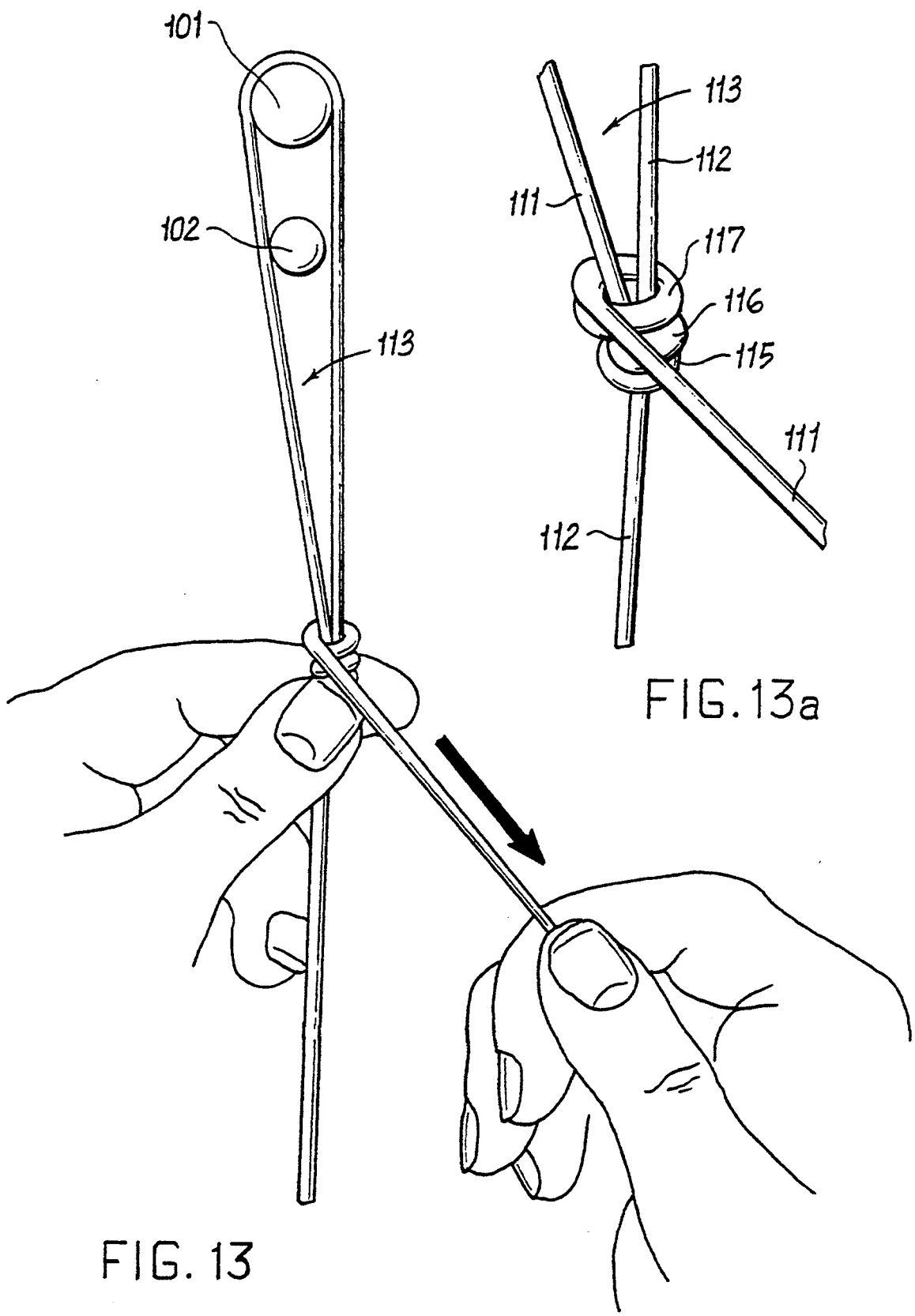

Referring to FIGS. 12 and 12a, suture portion 111 is then again brought around and under the primary loop forming sections of both portions 111 and 112, and crossed over the top of the knot to form a third turn 117. Suture portion 111 is then pulled taut as shown in FIGS. 13 and 13a.

Figures 14, 14A:
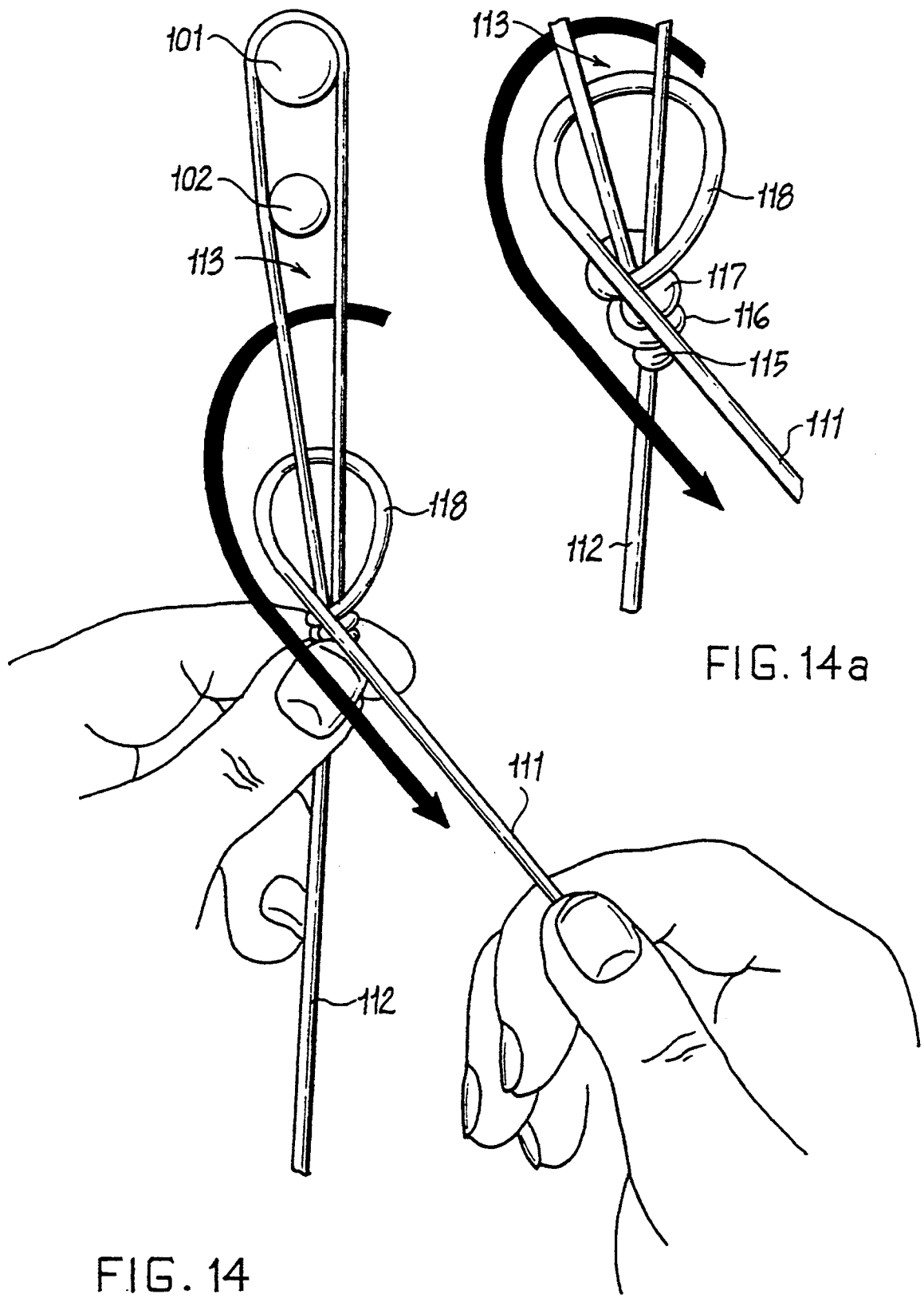
Figures 15, 15A:
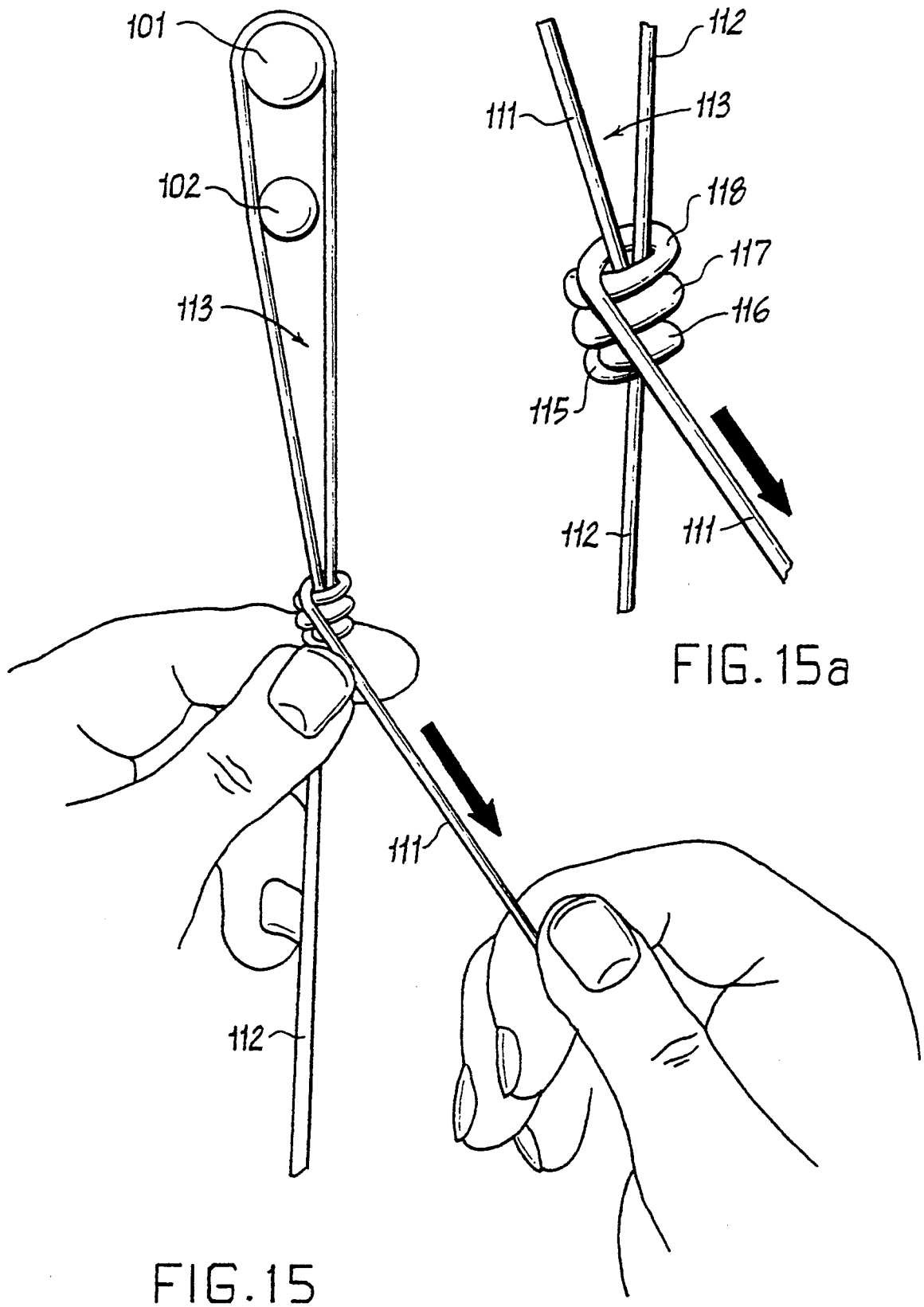

Referring to FIGS. 14 and 14a, suture portion 111 is then again brought around and under the primary loop forming sections of both portions 111 and 112, and crossed over the top of the knot to form a fourth turn 118. Suture portion 111 is then pulled taut as shown in FIGS. 15 and 15a.

Figures 16, 16A:
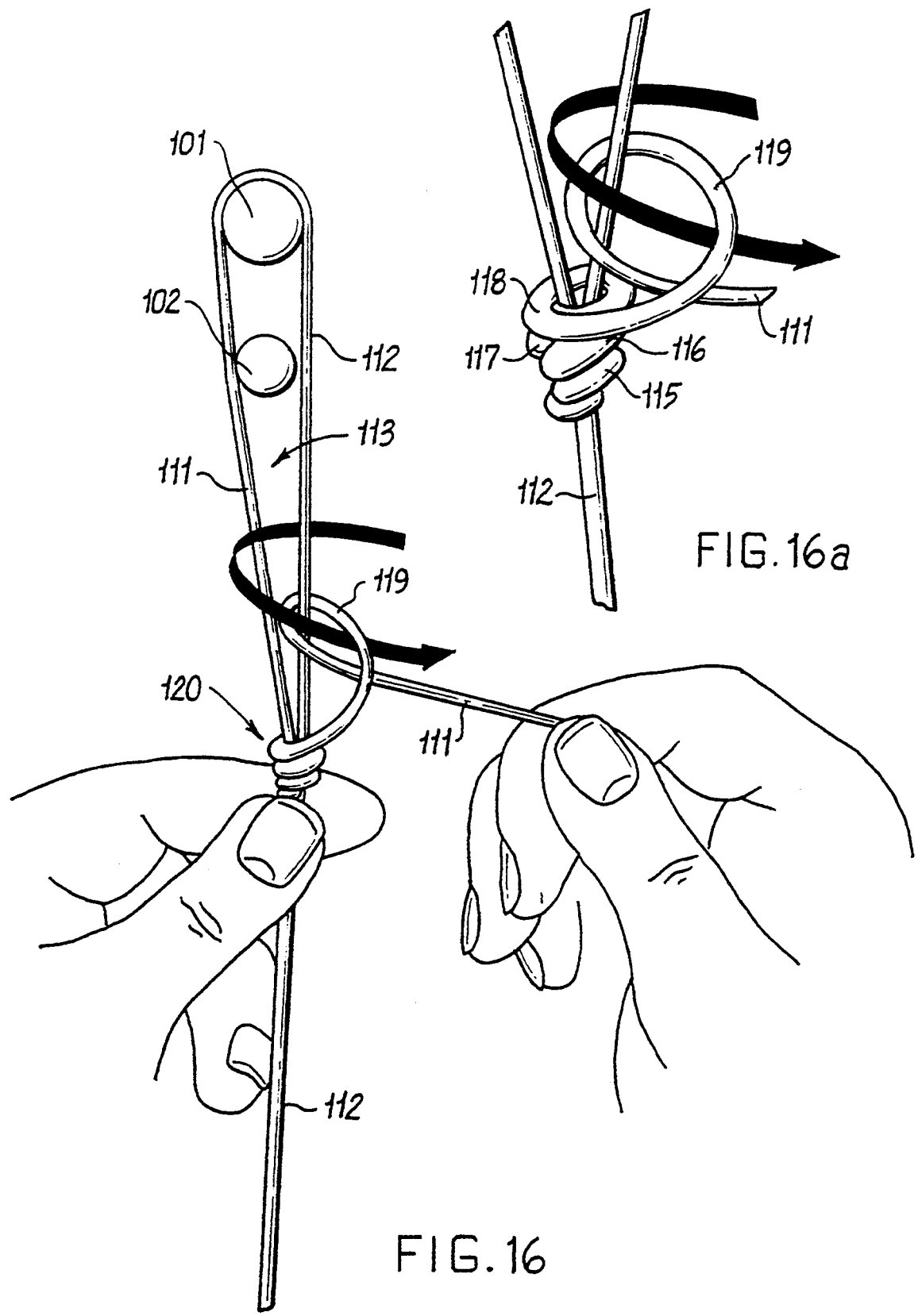
Figures 17, 17A:
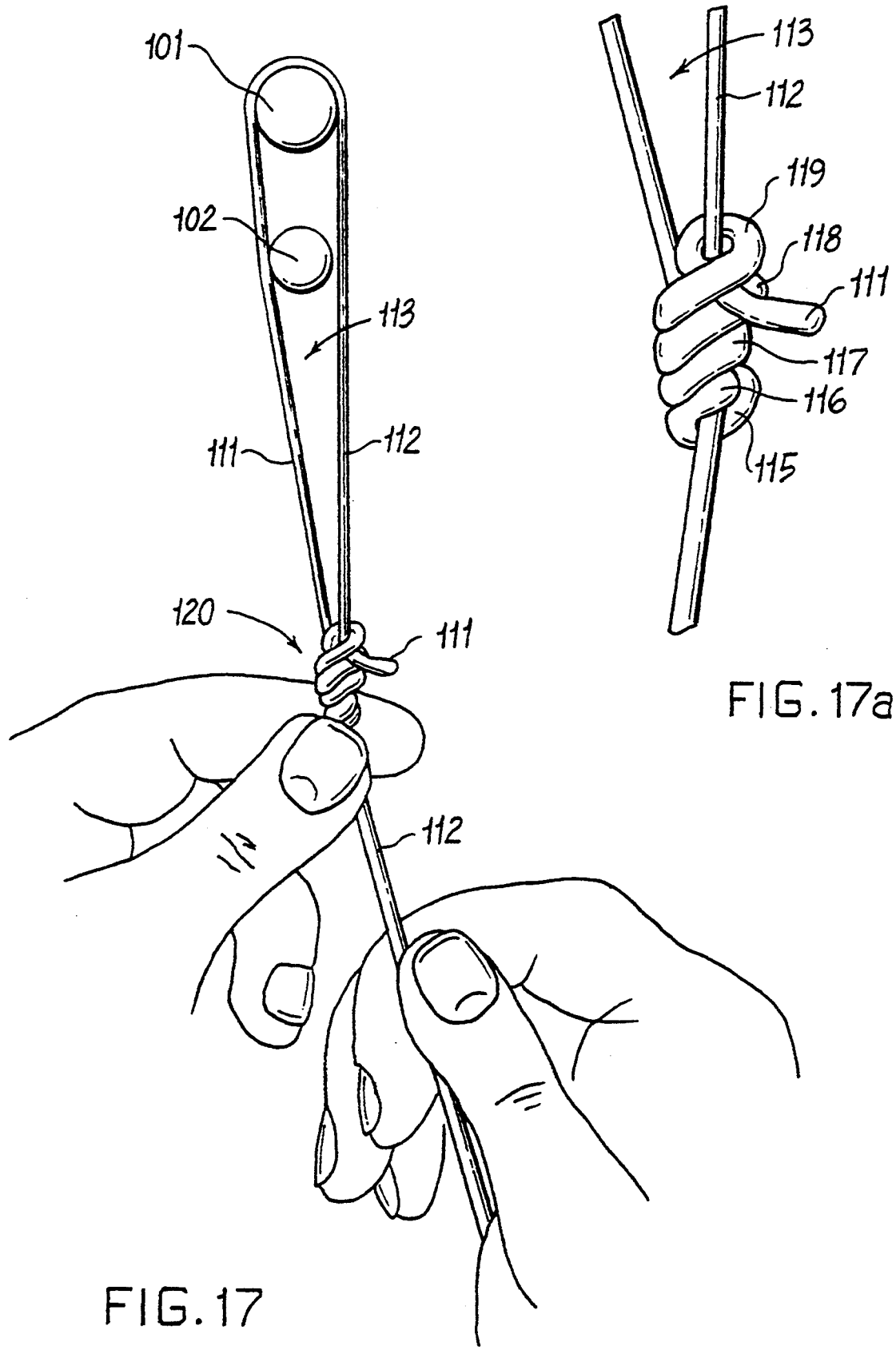

Referring to FIGS. 16 and 16a, suture portion 111 is then brought around and under the primary loop forming section of suture portion 112 and up through primary loop 113 to form a fifth turn 119. Suture portion 111 is then passed through fifth turn 119 to finish the knot 120 with a half-hitch around suture portion 112. Suture portion 111 is then pulled taut as shown in FIGS. 17 and 17a to tighten slip knot 120.

Figure 18:
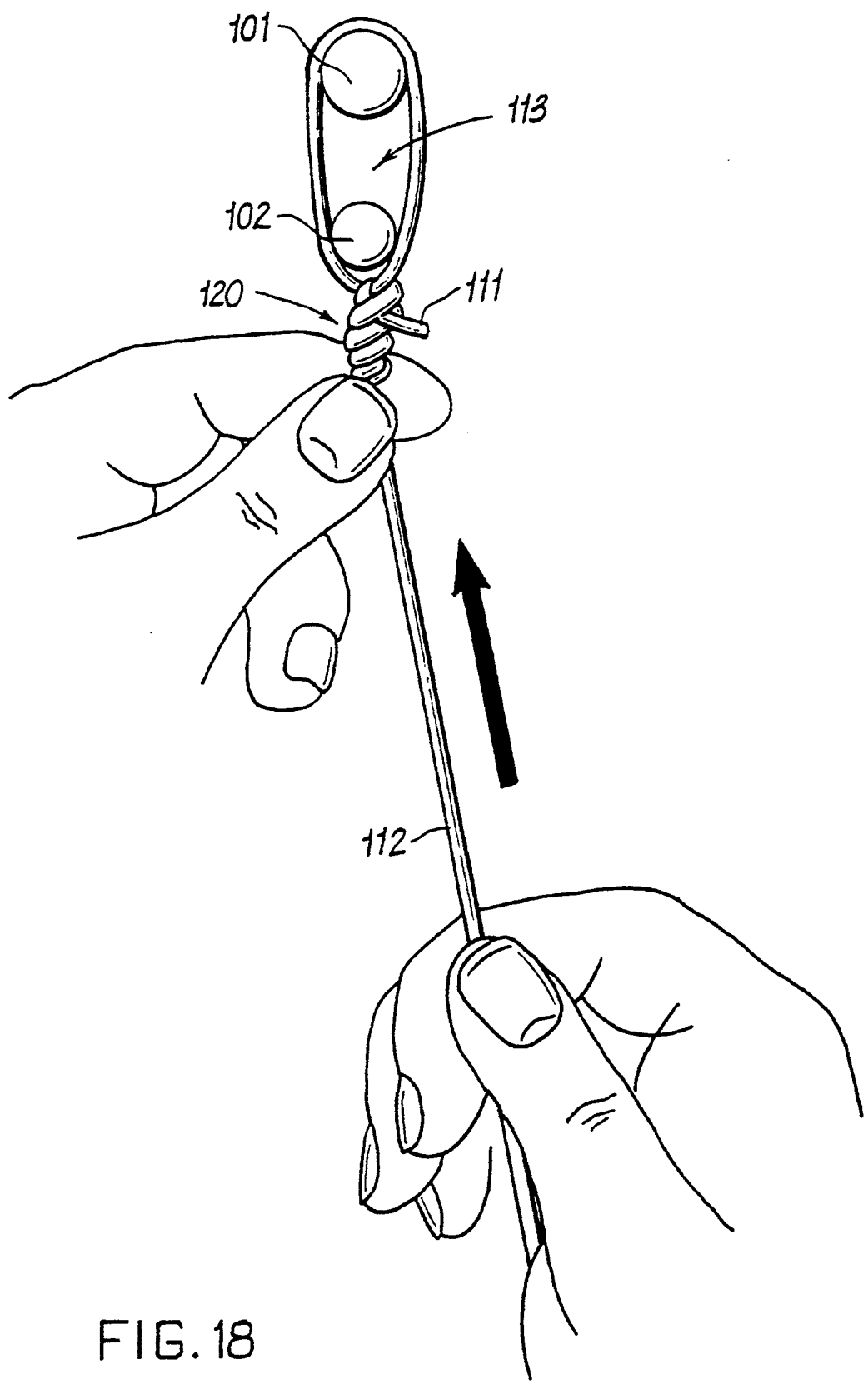

Referring to FIG. 18, slip knot 120 is then pushed along suture portion 112 up to mandrel 102. The spacing between members 101 and 102 and the diameter of the upright members determine the size of primary loop 113.

Figure 19:
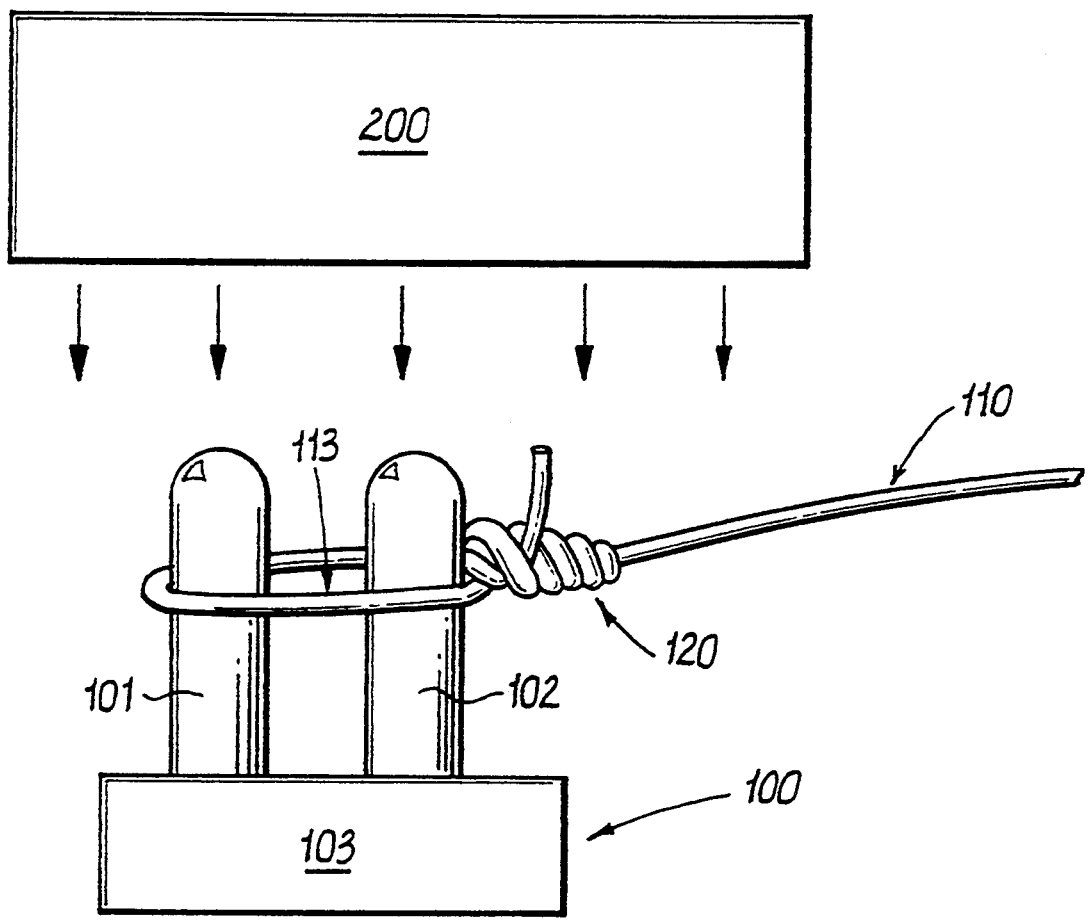
FIG. 19 illustrates diagrammatically the method for stiffening the knot by the heat setting method of the present invention.

Referring to FIG. 19, a source of hot air 200 having time and temperature controls is then used to direct a stream of air warmed to a predetermined temperature onto the looped end of the suture. Heat treatments can be performed on the running end 111 and the standing part 112, of the suture 110 as well as the knot 120 and loop 113. The predetermined temperature is the heat treating temperature discussed above. As discussed above, it is preferable to maintain a temperature within the given range for all diameters of sutures, and to vary the heating time: smaller diameter sutures require shorter heating times and larger diameter sutures require longer heating times. For a U.S.P. size 1/0 suture the temperature may be from between about 300° F. to about 320° F., and the duration of heating may be from about 4 seconds to about 6 seconds. Timing should preferably run from the point at which the suture reaches the heat treatment temperature.

Table II below sets forth a tabulation of heating times for various size sutures at the preferred heating temperature of 320° F.

TABLE II

| Glycolide/lactide suture Heat Treating Temperature = 320° F. | |
| --- | --- |
| Suture Size | Heating Time (seconds) |
| 2 | 6–8 |
| 1 | 5–6 |
| 1/0 | 4–6 |
| 2/0 | 3–5 |
| 3/0 | 2–3 |
| 4/0 | 1–2 |
| 5/0 | 1–2 |

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for reversibly stiffening a looped and knotted suture, comprising heating the looped portion of the suture to a predetermined temperature and maintaining said temperature for a period of time, said predetermined temperature and said time period being sufficient to cause the looped portion of the suture to be reversibly stiffened upon being permitted to cool.

2. The method of claim 1, wherein the suture is looped and knotted around a mandrel.

3. The method of claim 2, wherein the mandrel includes two upright members to facilitate looping and knotting the suture.

4. The method of claim 1, wherein said predetermined temperature is from about 300° F. to about 320° F.

5. The method of claim 4, wherein said period of time is from about 1 to about 8 seconds.

6. The method of claim 5, wherein said period of time is determined in accordance with suture size as follows:

| Suture Size | Heating Time (seconds) |
|---|---|
| 2 | 6–8 |
| 1 | 5–6 |
| 1/0 | 4–6 |
| 2/0 | 3–5 |
| 3/0 | 2–3 |
| 4/0 | 1–2 |
| 5/0 | 1–2 |

7. The method of claim 1, wherein said suture loop is formed by looping and knotting the suture in accordance with a procedure comprising:
   a) providing a suture thread having first and second end portions;
   b) forming a bight and passing said first end portion over said second end portion to form a primary loop; and
   c) forming a knot to secure said primary loop.

8. The method of claim 7, wherein said knot is formed by passing said first end portion around said second end portion and then through said primary loop to form a first turn encircling said second end portion, and then passing said first end portion under and around both the second and first end portions at least once to form at least one turn for encircling both the first and second end portions, then passing said first end around said second end portion to form a final turn, passing said first end portion through said primary loop, and then through said final turn.

9. The method of claim 7, wherein said knot is formed by making a turn of the first end portion around the second end portion, making at least one intermediate turn of the first end portion around the loop forming portions of both the first end portion and the second end portion, and terminating the knot with a half hitch.

10. The method of claim 1, wherein said suture is fabricated from a bioabsorbable material.

11. The method of claim 10, wherein said bioabsorbable material is a polymer selected from the group consisting of homopolymers and copolymers of glycolide, lactide, caprolactone, p-dioxanone, trimethylene carbonate, and combinations thereof.

12. The method of claim 1, wherein said suture is fabricated from a non-bioabsorbable material.

13. The method of claim 12, wherein said non-bioabsorbable material is selected from the group consisting of cotton, dacron, linen, silk, nylon, and polypropylene.

14. A method for reversibly stiffening a looped and knotted suture comprising heating the knotted portion of the suture to a predetermined temperature and maintaining said temperature for a period of time, said predetermined temperature and said time period being sufficient to cause the knotted portion of the suture to be reversibly stiffened upon being permitted to cool.

15. A suture having first and second end portions which includes a loop formed from said first and second end portions and a slidable knot for securing said loop wherein said knot includes a turn of the first end portion around the second end portion, at least one intermediate turn of the first end portion around the loop forming portions of both the first end portion and the second end portion, and a half hitch for securing the knot, wherein said looped and knotted suture is reversibly stiffened by heating said suture to a temperature of from about 300° F. to about 320° F. for a duration of time sufficient to cause said suture to be reversibly stiffened upon being cooled.

16. The suture of claim 15, wherein said knot includes at least two intermediate turns of the first end portion around the loop forming portions of both the first end portion and the second end portion.

17. The suture of claim 15, wherein said knot includes from 2 to about 6 intermediate turns of the first end portion around the loop forming portions of both the first end portion and the second end portion.

18. The suture of claim 15, wherein said half hitch is formed by said first end portion around said second end portion.

19. The suture of claim 15, including at least two intermediate turns.

20. The suture of claim 15, including at least four intermediate turns.

21. The suture of claim 15, including at least six intermediate turns.

* * * * *